United States Patent [19]

Tarr et al.

[11] Patent Number: 5,395,304
[45] Date of Patent: Mar. 7, 1995

[54] ACTIVE PIVOT JOINT DEVICE

[76] Inventors: Stephen E. Tarr, 1706-4 Somerset Pl., Louisville, Ky. 40220; J. Scott Newfield, 1115 Hickory Dr., Broken Arrow, Okla. 74012

[21] Appl. No.: 44,368

[22] Filed: Apr. 6, 1993

[51] Int. Cl.6 .............................................. A61F 3/00
[52] U.S. Cl. ..................... 602/26; 602/16; 602/20; 602/23
[58] Field of Search ............... 602/16, 26, 20, 23, 602/5; 128/25 R; 482/121, 124, 128

[56] References Cited

U.S. PATENT DOCUMENTS

| | | |
|---|---|---|
| 3,976,057 | 8/1976 | Barclay . |
| 4,433,679 | 2/1984 | Mauldin et al. ............ 602/16 |
| 4,436,303 | 3/1984 | McKillip . |
| 4,718,865 | 1/1988 | Airy . |
| 4,801,138 | 1/1989 | Airy . |
| 5,013,037 | 5/1991 | Stermer . |
| 5,020,797 | 6/1991 | Burns . |
| 5,052,375 | 10/1991 | Stark . |
| 5,052,379 | 10/1991 | Airy . |
| 5,074,549 | 12/1991 | Harvey . |
| 5,116,296 | 6/1992 | Watkins . |
| 5,135,469 | 8/1992 | Castillo . |

*Primary Examiner*—Richard J. Apley
*Assistant Examiner*—Beverly A. Meindl

[57] ABSTRACT

An addition (20) to a pivot joint or pivot hinge device, more specifically to a rehabilitative pivot joint brace (10), either within the manufacturing process or as a suitable attachment, which provides the ability to bias or resist the rotation of the pivot joint when such a resistive force would be beneficial. The addition (20) is suitably attached to a pivot joint device (14) composed of an upper frame section (16) connected to a lower frame section (18) by a pivot joint assembly (26) which enables the upper and lower frame sections to pivot about a transverse axis (12). The addition (20) produces a desired level of resistance to the flexion and extension of the body joint and in a determined degree of equilibrium through the combined efforts of a tension control assembly (30) and an equilibrium control assembly (28) which are associated by a connection (36). The selectively adjustable levels of resistance to the flexing and extending of the body joint are provided by the tension control assembly (30) which is suitably attached to the lower frame section (18) of the pivot joint device (14). The degree of equilibrium, that is the angle at which the rotational resistance is at rest, is regulated by the equilibrium control assembly (28) which is suitably attached to the pivot joint assembly (26) in alignment with the transverse axis of rotation (12). A change in this degree of equilibrium will result in more resistance to flexion and less resistance to extension or to the contrary or to an equal amount of resistance to both while the present invention is in use. During such periods of use, the body joint is exercised simply by the flexing and the extending of the joint.

22 Claims, 5 Drawing Sheets

ACTIVE PIVOT JOINT DEVICE

FIELD OF THE INVENTION

The present invention concerns pivot joint or pivot hinge devices, and more particularly, an addition, either by attachment or through the manufacturing process, to such devices, including any stabilizing or rehabilitative body joint brace composed of an upper and lower section and a pivot joint assembly, where the ability to bias or resist the rotation of the pivot joint would be beneficial.

BACKGROUND—DISCUSSION OF PRIOR ART

Exercise and physical fitness are a permanent part of life for millions of people in today's world. While some forms of exercise are more vigorous than others, every form of exercise brings with it the possibility of injury. Accompanying the steady increase in fitness activities over the last decade are an increasing number of musculoskeletal injuries being reported. Many injuries of this kind require surgical restoration of the damaged muscles, tendons, ligaments and other body components especially when a body joint such as the knee, elbow, shoulder, ankle, or wrist is involved. Following surgery to repair a body joint, the patient typically returns to normal activity only after enduring a long and structured program of rehabilitation. The rehabilitation process generally involves constant stabilization and support of the injured joint along with a gradually demanding program of therapy and exercise to strengthen the surrounding muscles and return flexibility to the repaired ligaments. Most programs consist of simple flexion and extension of the body joint and some applied resistance as the injured joint permits. These rehabilitative exercises are customarily performed within a controlled line and range of motion with the resistance level being increased over time. This is to help prevent any further injury and to prevent the joint from bearing too much stress before it is ready.

The stability and mobility of the injured joint is often controlled by the constant wearing of a brace or similar appliance generally consisting of coupled frames made up of an upper and lower section and a pivot joint. These braces are designed to be carried entirely by the body with the pivot joint generally coinciding with the anatomical pivot axis of the associated body joint. Throughout the beginning stages of the recovery, the patient may be required to wear a stabilizing brace during all times of activity, even for normal movement. Then, as the injured joint is strengthened, the brace becomes necessary only for more strenuous exercises. Although the bracing devices do provide stability and thus help facilitate the recovery of the joint, the brace itself has no muscle building effects.

Normally, the rehabilitative treatment program is designed and administered by a physical therapist often with all of the exercises being presided over at a special facility or clinic utilizing sophisticated, complex equipment that requires supervision and instruction. Possible machines found in these specialized clinics are disclosed in U.S Pat. Nos. 4,436,303 to McKillip (1984), 5,020,797 to Burns (1991), and 5,074,549 to Harvey (1991). With this type of program the patient must make special considerations to deal with travel and time conveniences in order to complete a proper recovery. Even when patients are allowed to preside over some or all of the exercises on their own, the recommended exercises are often inefficient and awkward to perform, such as lifting sandbags, working out with surgical tubing, and self-administered stretching. As a consequence of these burdens, physical therapy, one of the most important steps for the adequate recovery of the injured joint, is often missed or performed improperly, which leaves the joint unstable and more susceptible to reinjury. An incomplete or poorly followed program often leads to a poor or incomplete recovery.

Some more appropriate appliances have been developed for exercising and rehabilitating injured joints. Such devices typically include an upper and lower arm or section rotationally connected with a pivot joint assembly. These devices are designed to be suitably attached to the body in conjunction with the injured joint and to utilize a resistance mechanism to bias the relative movement of the pivot arms and thus impart a resistance force against movement of the body joints. Examples of such devices are disclosed in U.S. Pat. Nos. 3,976,057 to Barclay (1976), 4,718,665 to Airy and Kadavy (1988), 4,801,138 to Airy and Kadavy (1989), and 5,013,037 to Stermer (1991), as well as 5,052,375 to Stark (1991), 5,052,379 to Airy and Kadavy (1991), 5,116,296 to Watkins (1992) and 5,135,468 to Meissner (1992). While they are adapted to be mounted on the body, some of these devices are still too cumbersome to be worn continually during normal activity and some do not allow any adjustability of the resistance mechanism tension level or its angle of equilibrium. The ability to control the angle at which the resistance mechanism is in equilibrium allows the muscles used for flexion and the muscles used for extension of the joint to be exercised differently. Thus, depending on the injury, either the flexion or the extension of the joint can be emphasized and in varying amounts. The resistance tension level should be adjustable to control the force of resistance applied to the joint. Those devices which do possess adjustability make it awkward and inefficient to change their setup. The apparatus in U.S. Pat. No. 5,052,379 to Airy and Kadavy (1991) even necessitates removing and changing certain parts. The adjustable devices are also extremely complex and require elaborate and intricate manufacturing procedures such as those in U.S. Pat. Nos. 5,052,375 to Stark (1991) and 5,116,296 to Watkins (1992). The nature of their design also dictates that these adjustable rehabilitative devices be manufactured as a whole unit thus eliminating the possibility of quickly adapting the concept to a wide range of brace and pivot joint designs.

OBJECTS AND ADVANTAGES

Accordingly, it is a primary object of the present invention to provide an addition to a pivot joint device, either within the manufacturing process or as a suitable attachment, which may benefit from a resistance to the rotation of the pivot joint.

It is a further object of the present invention to provide a means of adjustment for the tension level applied by the resistance unit and a means of adjustment for the angle degree at which the resistance unit is in equilibrium. The methods of adjustment are efficient and easy and do not require any interchanging pans or pieces. With the ability to adjust the tension level of the resistance mechanism, the present invention may apply different amounts of resistance to the rotation of the pivot joint. Also, with the ability to adjust the angle at which the resistance unit is in equilibrium, the present invention will allow for varying amounts of resistance to be applied to the flexure as well as the extension of the pivot joint.

It is a further object of the present invention to provide a simple addition to a pivot joint device which will apply rotational resistance to the pivot joint such that it may be quickly adapted to any design of such a pivot joint device. Many different designs of rehabilitative pivot joint braces have been developed to accommodate the fact that most body joints approximate but are not exactly analogous to a simple pivot or hinge joint. This addition to the pivot joint device is independent of the entire appliance which utilizes the pivot joint device and is not required by design to be manufactured as an integrated piece of a unit. It also involves a simplistic design and thus a much simpler manufacturing process.

It is another object of the present invention to provide an addition to a pivot joint device which can continually resist the rotational movement of the pivot joint while the pivot joint device is being utilized during normal activity. In a preferred embodiment the present invention may be worn continuously as a rehabilitative and muscle building element for the benefit of an injured or weakened body joint. The present invention is functional and will not interfere with ordinary movement. It is also useful by providing a constant resistance to the pivot joint rotation and thus persistent exercise of the recovering muscles and ligaments of the injured body joint.

BRIEF DESCRIPTION OF THE DRAWINGS

The details of typical embodiments of the present invention will be described in connection with the accompanying drawings, in which.

LIST OF REFERENCE NUMERALS:

10 rehabilitative pivot joint brace
12 transverse axis of rotation
14 pivot joint device
16 upper frame section
18 lower frame section
20 addition to a pivot joint device
26 pivot joint assembly
28 equilibrium control assembly
30 tension control assembly
32 tension control assembly frame
34 tension adjustment assembly
36 connecting mean
38a and 38b biasing means
40 tension adjustment piece
42 tension indicator head
44 adjustment piece base
46 threaded stabilizing piece
47 assembly frame opening
48 threaded adjustment piece path
50 equilibrium assembly support
52 attachment base
53 coil spring
54 coil containment housing
56 coil containment chamber
58 pull-out pin guiding chamber
60 threaded pull-out pin
62 pull-out pin base
64 pull-out pin leg
66 equilibrium assembly head
67 rotating base
68 equilibrium angle holder
70a and 70b locking pins
72 locking holes
74a and 74b stopping guards
76 pull-out pin path

DETAILED DESCRIPTION—FIGS. 1 to 5B

Figure 1:
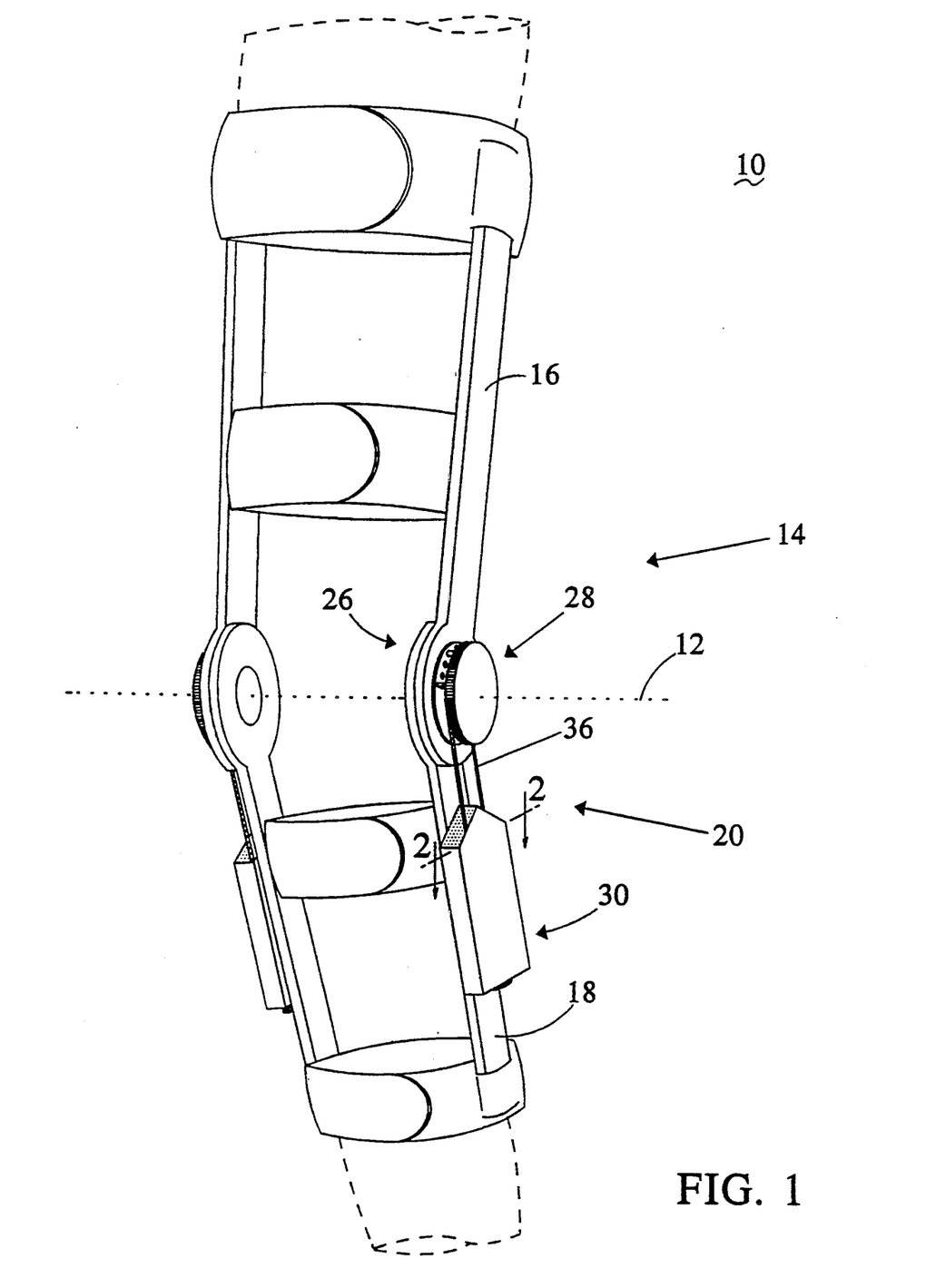
FIG. 1 is an isometric view of the present invention adapted to exercise the knee joint as an attachment to the pivot joint of a rehabilitative knee brace.
Figure 2:
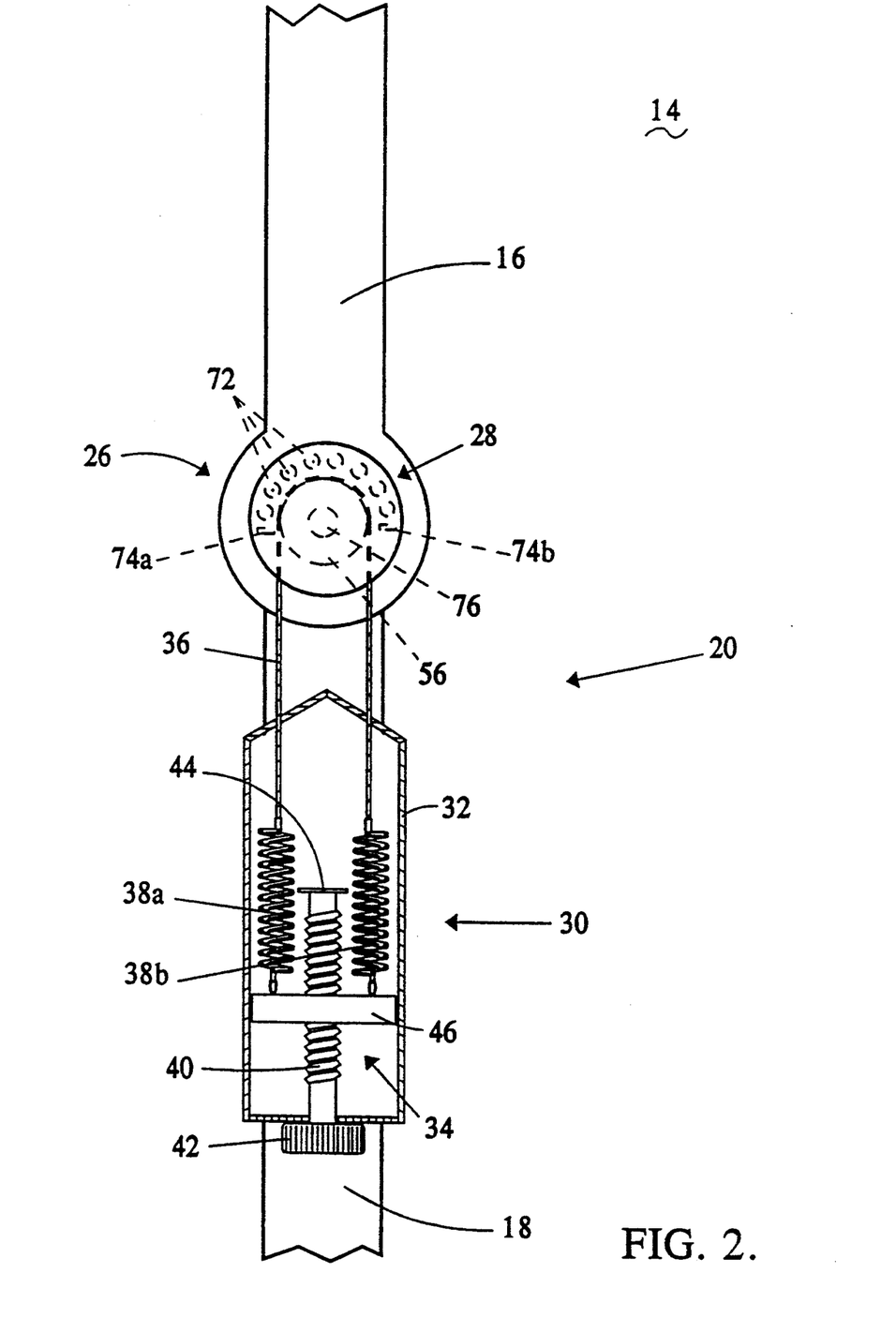
FIG. 2 is an enlarged, fragmentary, partial cross sectional view of the present invention shown in FIG. 1 and taken substantially along lines 2—2 thereof.

Referring initially to FIGS. 1 and 2, an addition 20 to a rehabilitative pivot joint brace 10, either within the manufacturing process or as a suitable attachment, which provides the ability to bias or resist the rotation of a pivot joint is illustrated for use in conjunction with a knee joint brace. However, it is to be understood that the present invention may be adapted for use in conjunction with other rehabilitative body joint braces including the ankle, elbow, or wrist, as well as with other pivot joint devices. As shown in FIG. 1, in basic form, the addition 20 is attached to a pivot joint device 14 composed of an upper frame section 16 connected to a lower frame section 18 by a pivot joint assembly 26 which enables the upper and lower frame sections to pivot about a transverse axis 12. The axis 12 is positioned in approximate alignment with the axis of rotation of the knee joint by the pivot joint brace 10 which is designed to be attached to the leg and carried entirely by the body. It will be appreciated that, when used in conjunction with a rehabilitative body joint brace 10, as in this case, an addition 20 may be mounted on the pivot joint device 14 on both sides of the brace 10. By adding to both sides of the brace 10, an unequal resistance load is not imposed on the body joint.

The addition 20, shown in more detail in FIG. 2, produces a desired level of resistance to the flexion and extension of the body joint and in a determined degree of equilibrium through the combined efforts of a tension control assembly 30 and an equilibrium control assembly 28 which are associated by a connecting means 36. The selectively adjustable levels of resistance to the flexing and extending of the body joint are provided by the tension control assembly 30 which is suitably attached to the lower frame section 18 of the pivot joint device 14. The degree of equilibrium, that is the angle at which the means of rotational resistance are at rest, is regulated by the equilibrium control assembly 28 which is suitably attached to the pivot joint assembly 26 in alignment with the transverse axis of rotation 12. A change in this degree of equilibrium will result in more resistance to flexion and less resistance to extension or to the contrary or to an equal amount of resistance to both while the present invention is in use. During such periods of use, the body joint is exercised simply by flexing and extending the leg. The aforementioned attachments may be comprised of any suitable securing device such as bolts, clips, clamps, rivets, welding, or adhesives which would not impair the normal function of the pivot joint device 14 or the pivot joint assembly 26. The attachment procedure may be designed to be part of any pivot joint device: manufacturing process or as a task which can be completed after the manufacturing process of any pivot joint device or any pivot joint brace. The following will describe the construction and operation of the active addition 20 to the pivot joint assembly 14 in more detail.

Figure 3:
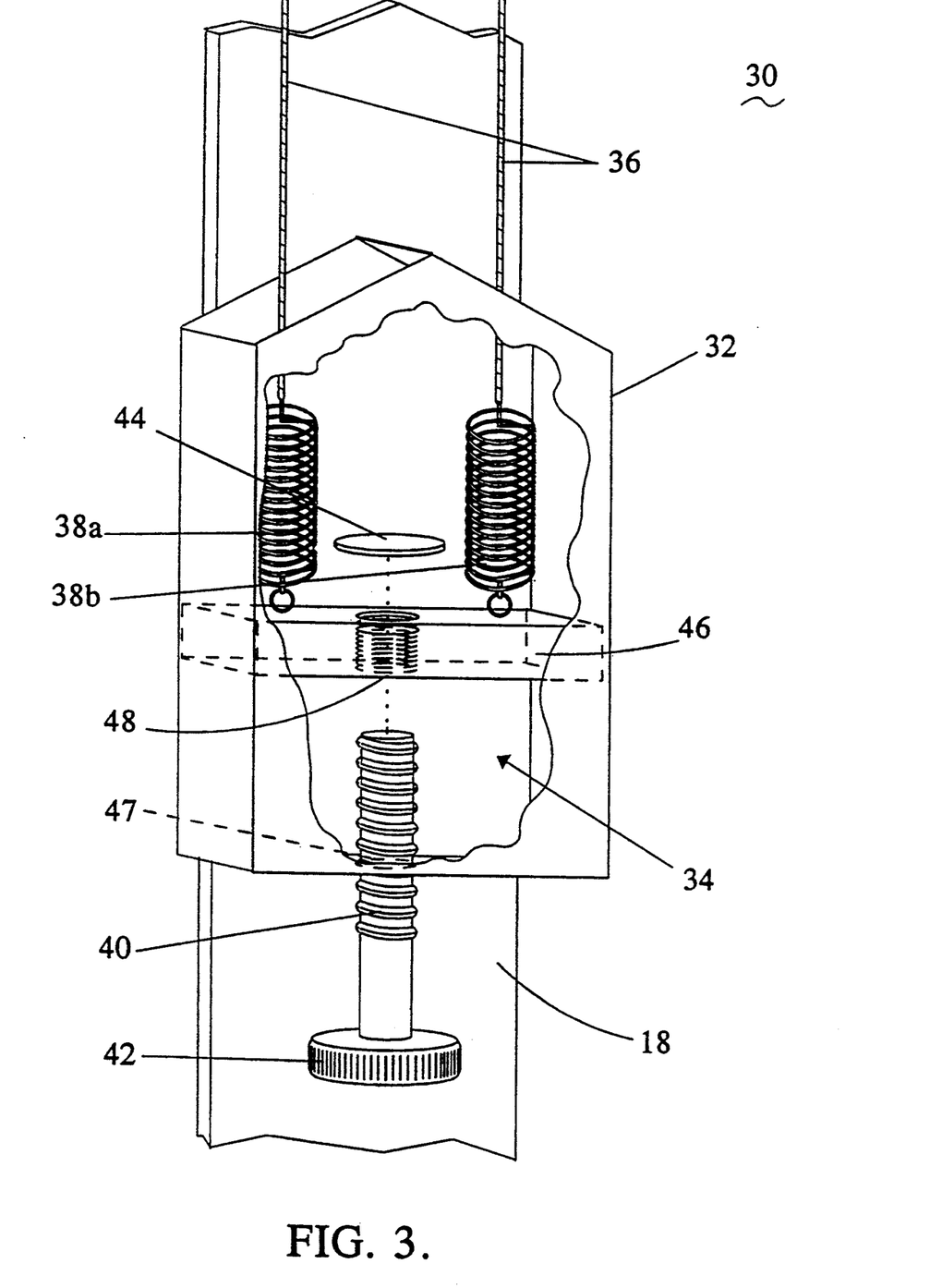
FIG. 3 is a fragmentary, isometric view of the tension resistance unit shown in FIG. 2 with portions broken away and exploded.

Considering the construction of the tension control assembly 30, as shown in FIG. 3, this tension control assembly 30 includes a tension adjustment assembly 34 which is largely enclosed by a tension control assembly frame 32. This tension control assembly frame 32 is suitably attached to the pivot joint device 14 on the lower frame section 18 which resembles a flat, elongated arm extending downward from the enlarged, circular pivot joint assembly 26. The tension adjustment assembly 34 includes a rotating adjustment piece 40 which is inserted into the tension control assembly frame 32 through the assembly frame opening 47 and screwed through the threaded stabilizing piece 46 via the threaded adjustment piece path 48. As the rotating adjustment piece 40 is turned, the threaded stabilizing piece 46 will move up or down within the tension control assembly frame 32 depending upon the direction of the turning motion. Two separate biasing means 38a and 38b, shown here as coil springs, are suitably attached to the upper side of the threaded stabilizing piece 46 on their lower ends. Their upper ends are attached, one each, to the ends of the connecting means 36 which extends up from one biasing means 38a, over the stationary equilibrium control assembly 28, and back down to the other biasing means 38b. It will be appreciated that the forced extension of these biasing means 38a and 38b causes a natural tension as they physically strain to return to their original compacted state. This level of tension will vary as the stabilizing threaded piece 46 moves towards or away from the equilibrium control assembly 28 due to the rotating action of the tension adjustment assembly 34. An adjustment piece base 44 is suitably attached to the rotating adjustment piece 40 after insertion to prevent the threaded stabilizing piece 46 from disembarking from the rotating adjustment piece 40 as the level of resistance is modified. The tension indicator head 42 keeps the rotating adjustment piece 40 positioned within the tension control assembly frame 32 by abutting against the lower portion of the anchored tension control assembly frame 32. The circular head piece 42 may be marked to indicate the level of resistance being created by the biasing means 38a and 38b. The biasing means 38a and 38b may consist of any suitable material capable of repeated expansion and contraction without noticeable wear. Such materials include metal or plastic springs, hard rubber, surgical tubing or bungee-like material, or any other material which resists being expanded or stretched and comes in numerous sizes and tensions as desired. The tension control assembly frame 32 may consist of any enclosing material suitably strong enough to secure attachment to a pivot joint device 14 and to support the resistance load created by the combined efforts of the biasing means 38a and 38b and the tension adjustment assembly 34. The connecting means 36 must consist of any material flexible enough to unwrap from and wrap around the design of the equilibrium control assembly 28 during operational rotation of the pivot joint device 14. This material must also be suitably strong enough, such as cable, wire, rope, or other fibrous strands, to withstand the load created by the forced expansion of the biasing means 38a and 38b.

Figure 4:
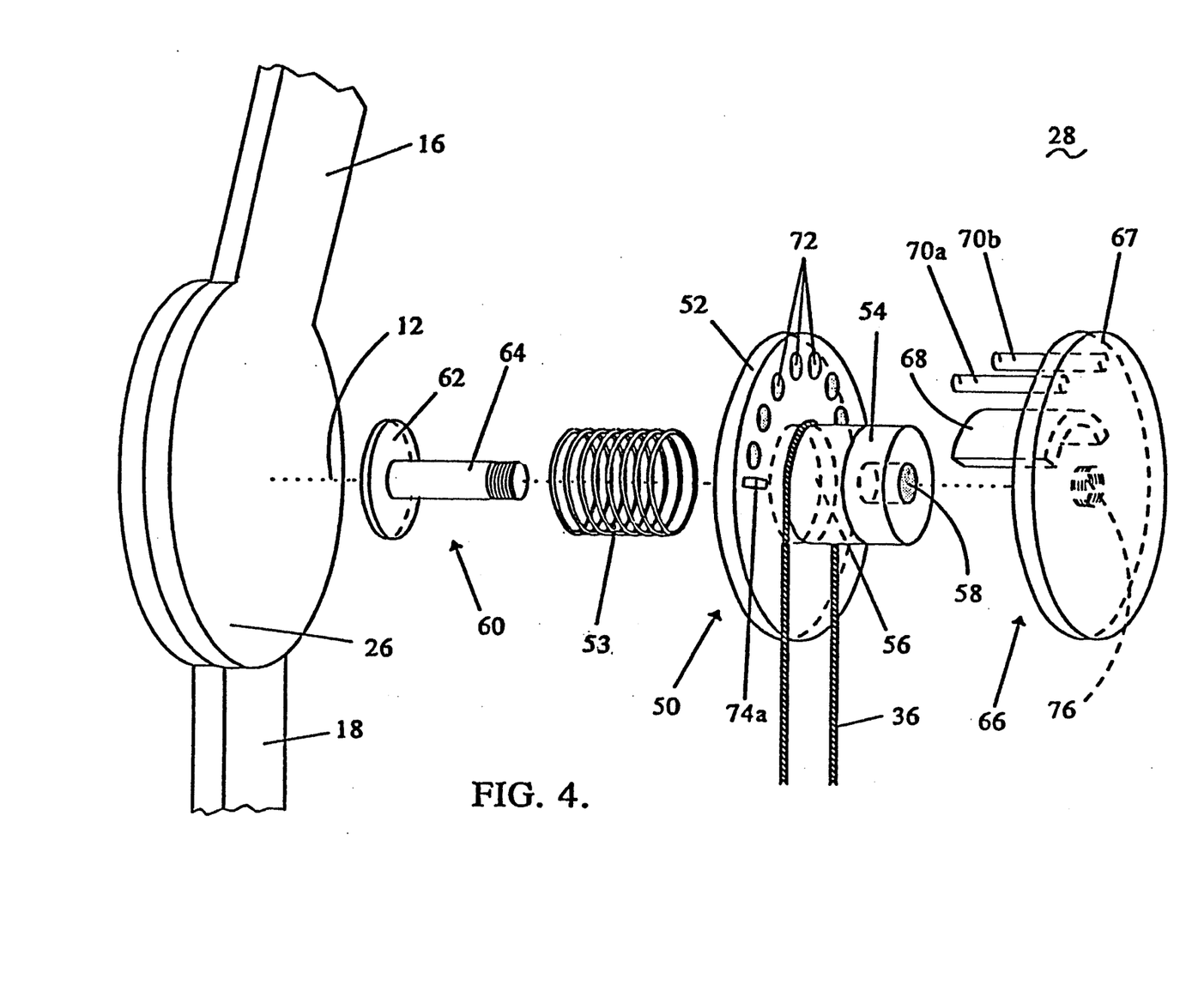
FIG. 4 is a fragmentary, isometric view of the equilibrium control assembly shown in FIG. 2 with certain components exploded.

The preferred form of the equilibrium control assembly 28, as illustrated in FIG. 4, is formed in part by an equilibrium assembly support 50 which has a cylindrical coil containment housing 54 protruding from a flat, circular attachment base 52. The coil containment housing 54 forms a hollow coil containment chamber 56 and is enclosed on the protruded end by a solid portion containing a circularly formed aperture, or pullout pin guiding chamber 58, in the center. A coil spring 53 is inserted into the hollow cavity of the coil containment device 54 followed by a threaded pullout pin 60 which has a long, threaded leg 64 and a circumferentially larger base 62. The pullout pin leg 64 is formed to fit through the middle of the coil spring 53 and to be closely receivable within the pullout pin guiding chamber 58. As a result, the coil spring will abut against the enclosed end of the coil containment chamber 56 on one side and against the pullout pin base 62 on the other. It will be appreciated that the threaded pullout pin 60 may be pushed or pulled through the pullout pin guiding chamber 56, thus compacting the coil spring 53, until the threaded end of the pullout pin leg 64 is fully exposed. The equilibrium assembly support 50 is suitably attached to the pivot joint assembly portion 26 of the pivot joint device 14 after the insertion of the coil spring 53 and the pullout pin 60 and in alignment with the transverse axis of rotation 12 of the pivot joint.

The equilibrium control assembly 28 is also formed by the equilibrium assembly head 66 which includes a flat, circular rotating base 67 containing a centrally located, threaded pullout pin path 76. The female threads of the pullout pin path 76 are designed to engage with the male threads on the pullout pin 60 thus connecting the equilibrium assembly head 66 to the equilibrium assembly support 50. The equilibrium assembly head 66 also has three fixtures protruding perpendicularly outward from the rotating base 67. The first is a curved equilibrium angle holder 68 sized to closely and rotatably engage with the outside of the protruding coil containment housing 54. In the preferred embodiment, the equilibrium angle holder 68 is designed to cover a quarter portion of the circumferential area of the coil containment housing 54 and to extend along its length. Thus, when the enclosed end of the coil containment housing 54 rests against the circumferentially larger rotating base 67 at the base of the equilibrium angle holder 68, the protruded end of the equilibrium angle holder 68 will also rest against the attaching base 52 at the base of the coil containment housing 54 in a quarter or ninety degree arc. By the foregoing construction, the tendency of the coil spring 53 to expand to its natural state of equilibrium within the coil containment housing 54 will continually pull the equilibrium assembly head 66 towards the equilibrium assembly support 50 until the protruded ends of both portions are at rest against the respective circular base portions.

The other two fixtures protruding from the rotating base 67 are diametrically opposed locking pins 70a and 70b designed to slightly exceed the length of the coil containment housing 54 and to be closely receivable with any of an array of spaced-apart locking holes 72 formed in the attaching base 52 of the equilibrium assembly support 50. These locking holes 72 follow a curved path that extends along the upper half of the attaching base 52 and they are flanked on both sides by two diametrically opposed stopping guards 74a and 74b. As discussed before, the center portion of the connecting means 36 extends up and over the equilibrium control assembly 28, more specifically the coil containment housing 54, while its ends remain attached to the biasing means 38a and 38b. In operation, the portion of the connecting means 36 which wraps up and over the coil containment housing 54 will also lay flat against the attaching base 52 at the base of the coil containment housing 54. As the protruded end of the equilibrium angle holder 68 abuts against the attaching base 52 it will also press inward on the connecting means 36 thus trapping a segment of the connecting means 36 against the attachment base 52. It will be appreciated that with the connecting means 36 anchored to the equilibrium control assembly 28, any rotation of the pivot joint assembly 26 will cause the forced expansion of one of the biasing means 38a or 38b thus creating a force of resistance to the rotation of the pivot joint assembly 26 in that direction. This construction also permits the contraction of the unopposed biasing means 38a or 38b thus preventing any slack from existing between the connecting means 36 and the biasing means 38a and 38b.

By the forgoing design of the equilibrium control assembly 28, the equilibrium assembly head 66 may, at any time, be pulled outward, away from the equilibrium assembly support 50, thus releasing the locking pins 70a and 70b from the locking holes 72 and freeing the connecting means 36 from an anchored state. The pivot joint device 14 may then be rotated slightly in either direction without forcing the expansion of the biasing means 38a and 38b. As the pivot joint device 14 is rotated without the connecting means 36 anchored to the equilibrium assembly support 50, the equilibrium angle of the addition 20, that is the angle at which the biasing means 38a and 38b are equally expanded, is altered. Changing the angle at which the addition to the pivot joint device 20 is in equilibrium will create a greater force of resistance to either the flexion of the body joint or to the extension of the body joint or will allow for an equal amount of resistance to both flexion and extension. Varied resistance in either extension or flexure may be desirable when recovering from certain types of injuries in which the flexion or extension muscles are damaged but not both. The stopping guards 74a and 74b are present to prevent the equilibrium assembly head 66 from revolving to a position where the locking pins 70a and 70b are not able to engage with the locking holes 72. It will be appreciated that in the present embodiment the biasing means 38a and 38b are both slightly expanded at all times once the addition 20 has been assembled as part of the pivot joint device 14. This will permit the contraction of the unopposed biasing means 38a or 38b and prevent any build-up of slack in the connecting means 36.

It will further be appreciated that the equilibrium control assembly 28 and the tension control assembly 30 may be of other configurations without departing from the spirit or scope of the present invention. For instance, the tension control assembly 30 may be constructed of any members capable of increasing or decreasing the tension on the biasing means 38a and 38b while these biasing means 38a and 38b are not in operation. This could also be achieved with a squeezable clip and slide assembly, not shown, where the threaded stabilizing piece 46 is moved towards or away from the equilibrium control assembly 28 after a locking device is unclipped, by squeezing on both sides, and then slid up or down within the tension control assembly frame 32. The equilibrium control assembly also may be constructed of any members which are suitably strong enough to secure attachment to the pivot joint device 14 and which are capable of being repeatedly secured and loosened to selectively anchor and release the connecting means 36, thus producing the desired result of altering the angle of equilibrium associated with the addition to the pivot joint 20. This can also be achieved with a female threaded equilibrium assembly support and a matching male threaded equilibrium assembly head, not shown, or with a spring loaded clamping device, also not shown.

Figure 5A:
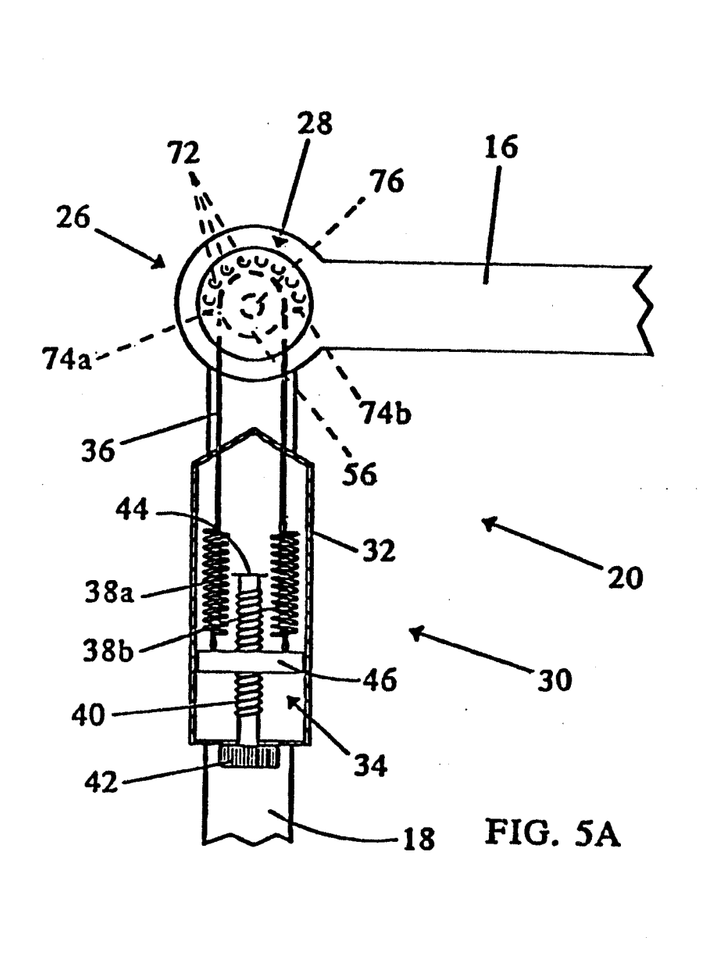
FIG. 5A is a fragmentary, partial cross sectional view of the present invention show in FIG. 1 illustrating the present invention in equilibrium at a desired angle.
Figure 5B:
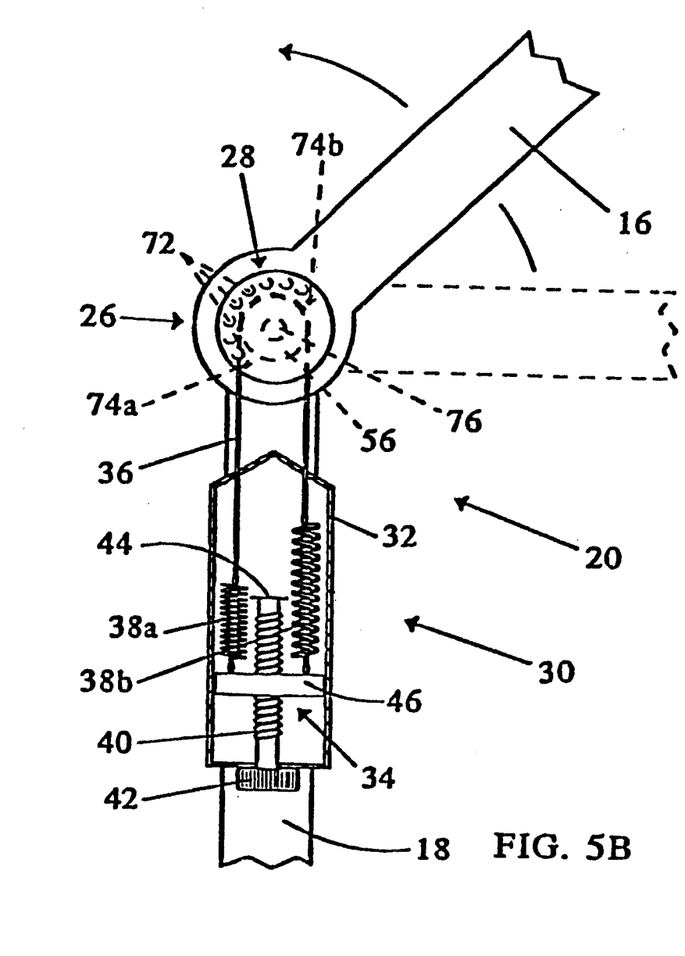
FIG. 5B is another fragmentary, partial cross sectional view of the present invention shown in FIG. 1 illustrating the movements of the present invention as the pivot joint is extended from its equilibrium position shown in FIG. 5A.

Next, referring specifically to FIGS. 5A and 5B, the operation of the addition 20 to a rehabilitative pivot joint brace 10 in the present embodiment will be illustrated in further detail. As shown in FIG. 5A, the tension control assembly 30 is set at a desired level of tension with the equilibrium control assembly 28 set to an angle which places the biasing means 38a and 38b at rest only when the pivot joint device 14 is in a fully flexed position. As the pivot joint device 14 is straightened to an extended position, shown in FIG. 5B, the connecting means 36 pulls on the biasing means 38b which is positioned to resist extension, thus forcing the expansion of this biasing mean 38b and creating a resistance to the rotation, specifically the extension, of the pivot joint device 14. Furthermore, as the pivot joint device 14 is rotated, portions of the connecting means 36 which have not been anchored by the equilibrium angle holder 68 will partially coil around one side of the coil containment housing 54 while simultaneously uncoiling from the opposite side thus allowing the other biasing means 38a, which is unopposed to extensional rotation, to contract. This compression of the unopposed biasing means 38a prevents any unwanted slack from forming in the connecting means 36. It will be appreciated that in the present embodiment, the extension of the knee joint is opposed, thereby exercising the quadracep muscles and stretching the surrounding knee ligaments and tendons to a fully flexed position through continual rotational resistance. If the angle of equilibrium were set such that the biasing means 38a and 38b were at rest only when the pivot joint device 14 was in a fully extended position, the flexion of the pivot joint would be opposed. In this instance, the hamstring and adductor magnus muscles would be exercised by the present invention as the forced bending of the pivot joint device 14 occurred. If the equilibrium control assembly 28 were set at any angle between the full extension and the full flexion of the pivot joint device 14, a resistance to rotation for both the bending and straightening of the pivot joint device 14 would be created. It will also be appreciated that the greater the level of tension set by the tension control assembly 30, the stronger the resistance imposed by the biasing means 38a and 38b on any rotation will be.

With the above-described construction, the present invention, may be conveniently adjusted to selectively and independently vary the levels of effort required to flex the leg and extend the leg. This is important in that the muscles used to extend the leg are substantially stronger than those used to flex the leg. Also by this construction, the active addition to a pivot joint device 20 may be utilized not only when performing specific exercises, but also during regular daily activities, whether at home or at work. As such, a specific time period does not have to be devoted to exercising a desired body joint, but rather the joint is exercised during normal body movements.

As will be apparent to those skilled in the art to which the invention is addressed, the present invention may be embodied in forms other than those specifically disclosed above and may be adapted for use with other body joints, such as ankle, wrist, or elbow joints without departing from the spirit or scope of the present invention. The particular embodiments of the addition to a pivot joint device 20 set forth above are therefore to be considered in all respects as illustrative and not restrictive. The scope of the present invention is as set forth in the appended claims rather than being limited to the examples of the active addition 20 set forth in the foregoing description.

The embodiments of the invention in which an exclusive property or privilege is claimed are defined as follows:

1. An augmentation for a pivot joint device having an upper and lower frame section and a pivot joint assembly comprising:
    a) tension control means for selectively imparting desired levels of resistance to the rotational movement of the pivot joint device;
    b) an equilibrium control means for selectively varying the angle at which the pivot joint device is in equilibrium where no resistance to rotational movement in either pivotal direction exists;
    c) means for mounting said tension control means on the lower frame section of the pivot joint device;
    d) means for mounting said equilibrium control means on the pivot joint assembly in approximate alignment with a pivot axis coinciding with the pivot axis of the pivot joint assembly; and
    e) means for connecting said tension control means and said equilibrium control means whereby the efforts of said tension control means and said equilibrium control means combine to bias the rotational movement of the pivot joint device in either pivotal direction.

2. The augmentation for a pivot joint device according to claim 1, said tension control means mounting means comprising:
    a) a box-like encasing structure and said tension control means comprising:
    b) an adjustable tension assembly substantially enclosed by said encasing structure having a female threaded adjusting piece engaged with a male threaded revolving piece whereby said adjusting piece is rotatably actuated by the rotation of said revolving piece thereby allowing said adjusting piece to move end to end on said revolving piece; and
    c) dual biasing means attached to said adjusting piece on one end and to said connecting means on the opposite end, said biasing means comprising elastic members which are displaced from their nominal condition by the rotation of the pivot joint device and which tend to return to their nominal condition when the load imposed on the pivot joint device is terminated.

3. The augmentation for a pivot joint device according to claim 1, said equilibrium control means further comprising:
    a) an attaching structure mountable on the pivot joint assembly comprising a hanging means whereby said connecting means may loop over said hanging means in a continual connection from one said biasing means to the other;
    b) a head structure connected to said attaching structure; and
    c) a securing means to selectively secure and release said head structure from an immobilized position in relation to said attaching structure.

4. The augmentation for a pivot joint device according to claim 3, wherein said securing means further comprising a trapping piece for capturing a selected portion of said connecting means between said attaching structure and said head structure when said securing means is in an immobile setting thereby forcing said connecting mean to behave as a permanent attachment to said equilibrium control means.

5. The augmentation for a pivot joint device according to claim 1, said connecting means further comprising a cable-like member attached on one end to one of said biasing means and following an uninterrupted path over said hanging means and attached on the other end to said other biasing means whereby said connecting means, when trapped by said equilibrium control means, will displace said biasing means from their nominal positions during any pivotal rotation of the pivot joint device thereby producing the resistance load on the rotational movement of the pivot joint device.

6. The augmentation for a pivot joint device according to claim 1, said means of mounting said tension control means comprising a fastening means whereby said tension control means may be suitably secured to the pivot joint device such that said fastening means withstand any resistance load imposed by rotation of the pivot joint device and that the normal action of the pivot joint device remains unimpaired.

7. The augmentation for a pivot joint device according to claim 1, said means of mounting said equilibrium control means comprising a fastening means whereby said tension control means may be suitably secured to said pivot joint assembly such that said fastening means withstand any resistance load imposed by rotation of the pivot joint device and that the normal action of the pivot joint device remains unimpaired.

8. An enhancement for a rehabilitative pivot joint brace having an upper and lower frame section and a pivot joint assembly comprising:
    a) tension control means for selectively imparting desired levels of resistance to the flexing and extending of a body joint;
    b) equilibrium control means for selectively determining the ratio between the degree of flexion and the degree of extension to be applied to said resistive force;
    c) means for mounting said tension control means on the frame sections of the pivot joint device;
    d) means for mounting said equilibrium control means on the pivot joint assembly in approximate alignment with a pivot axis coinciding with the pivot axis of the body joint; and
    e) means for connecting said tension control means and said equilibrium control means whereby said connecting means transmits the relative rotational movement of the pivot joint device to said tension control means to actuate said tension control means to generate a resistive load to the relative pivotal movement of the pivot joint device.

9. The enhancement for a rehabilitative pivot joint brace according to claim 8, said tension control means mounting means comprising:
   a) a box-like encasing structure and said tension control means comprising:
   b) an adjustable tension assembly substantially enclosed by said encasing structure and comprising a female threaded adjusting piece engaged with a male threaded revolving piece whereby said adjusting piece is rotatably actuated by the rotation of said revolving piece thereby allowing said adjusting piece to move end to end on said revolving piece; and,
   c) dual biasing means attached to said adjusting piece on one end and to said connecting means on the opposite end, said biasing means comprising elastic members which are displaced from their nominal condition by the rotation of the pivot joint device and which tend to return to their nominal condition when the load imposed on the pivot joint device by the body joint is terminated.

10. The enhancement for a rehabilitative pivot joint brace according to claim 8, said equilibrium control means comprising:
    a) an attaching structure mountable on the pivot joint assembly, said attaching structure further a comprising hanging means whereby said connecting means may loop over said hanging means in a continual connection from one said biasing means to the other;
    b) a head structure connected to said attaching structure; and
    c) securing means for selectively securing and releasing said head structure from an immobilized position in relation to said attaching structure.

11. The enhancement for a rehabilitative pivot joint brace according to claim 10, said securing means further comprising a trapping piece to capture a selected portion of said connecting means between said attaching structure and said head structure when said securing means is in an immobile setting thereby forcing said connecting means to behave as a permanent attachment to said equilibrium control means.

12. The enhancement for a rehabilitative pivot joint brace according to claim 8, said connecting means comprising a cable-like member attached on one end to one of said biasing means and following an uninterrupted path over said hanging means to be attached on the other end to said other biasing means whereby said connecting means, when trapped by said equilibrium control means, will displace said biasing means from their nominal positions during any pivotal rotation of the pivot joint device thereby producing the resistance load on the rotational movement of the pivot joint device.

13. The enhancement for a rehabilitative pivot joint brace according to claim 8, said means of mounting said tension control means comprising a fastening means whereby said tension control means may be suitably secured to the pivot joint device such that said fastening means withstand any resistance load imposed by rotation of the pivot joint device and that the normal action of the pivot joint device remains unimpaired.

14. The enhancement for a rehabilitative pivot joint brace according to claim 8, said means of mounting said equilibrium control means comprising a fastening means whereby said tension control means may be suitably secured to the pivot joint assembly such that said fastening means withstand any resistance load imposed by rotation of the pivot joint device and that the normal action of the pivot joint device remains unimpaired.

15. An addition to a rehabilitative pivot joint brace containing any number of pivot joint devices each having an upper and lower frame section and a pivot joint assembly comprising:
    a) tension control means disposed in a housing for selectively imparting desired levels of resistance to the flexing and extending of a body joint;
    b) equilibrium control means for selectively varying the angle at which the pivot joint device is in equilibrium where no resistance to rotational movement in either pivotal direction exists;
    c) means for mounting said tension control means housing on the lower frame section of the pivot joint device;
    d) means for mounting said equilibrium control means on the pivot joint assembly in approximate alignment with a pivot axis coinciding with the pivot axis of the body joint; and
    e) means for connecting said tension control means and said equilibrium control means whereby said connecting means transmits the relative rotational movement of the pivot joint device to said tension control means to actuate said tension control means to generate a resistive load to the relative pivotal movement of the pivot joint device.

16. The enhancement for a rehabilitative pivot joint brace according to claim 15, said tension control means further comprising:
    a) an adjustable tension assembly substantially enclosed by said housing and comprising a female threaded adjusting piece engaged with a male threaded revolving piece whereby said adjusting piece is rotatably actuated by the rotation of said revolving piece thereby allowing said adjusting piece to move end to end on said revolving piece; and
    b) dual biasing means attached to said adjusting piece on one end and to said connecting means on the opposite end wherein said biasing means include elastic members which are displaced from their nominal condition by the rotation of the pivot joint device and which tend to return to their nominal condition when the load imposed on the pivot joint device by the body joint is terminated.

17. The attachment to a rehabilitative pivot joint brace according to claim 15, said equilibrium control means further comprising:
    a) an attaching structure mountable on the pivot joint assembly, said attaching structure further comprising hanging means whereby said connecting means may loop over said hanging means in a continual connection from one said biasing means to the other;
    b) a head structure connected to said attaching structure; and
    c) securing means for selectively securing and releasing said head structure from an immobilized position in relation to said attaching structure.

18. The addition to a rehabilitative pivot joint brace according to claim 17, said securing means further comprising a trapping piece for capturing a selected portion of said connecting means between said attaching structure and said head structure when said securing means is in an immobile setting thereby forcing said connecting mean to behave as a permanent attachment to said equilibrium control means.

19. The addition for a rehabilitative pivot joint brace according to claim 15, said connecting means comprising a cable-like member attached on one end to one of said biasing means and following an uninterrupted path over said hanging means and attached on the other end to said other biasing means whereby said connecting means, when trapped by said equilibrium control means, will displace said biasing means from their nominal positions during any pivotal rotation of the pivot joint device thereby producing the resistance load on the rotational movement of the pivot joint device.

20. The addition for a rehabilitative pivot joint brace according to claim 15, said means of mounting said tension control means further comprising fastening means whereby said tension control means may be suitably secured to the pivot joint device such that said fastening means withstands any resistance load imposed by rotation of the pivot joint device and that the normal action of the pivot joint device remains unimpaired.

21. The addition to a rehabilitative pivot joint brace according to claim 15, said means of mounting said equilibrium control means further comprising fastening means whereby said tension control means may be suitably secured to the pivot joint assembly such that said fastening means withstands any resistance load imposed by rotation of the pivot joint device and that the normal action of the pivot joint device remains unimpaired.

22. An augmentation for a pivot joint device having an upper and lower frame section and a pivot joint assembly comprising:
   a) tension control means for selectively imparting desired levels of resistance to the rotational movement of the pivot joint device;
   b) an equilibrium control means for selectively varying the angle at which the pivot joint device is in equilibrium where no resistance to rotational movement in either pivotal direction exists;
   c) a housing containing said tension control means and mountable on the lower frame section of the pivot joint device;
   d) means for mounting said equilibrium control means on the pivot joint assembly in approximate alignment with a pivot axis coinciding with the pivot axis of the pivot joint assembly; and
   e) means for connecting said tension control means and said equilibrium control means whereby the efforts of said tension control means and said equilibrium control means combine to bias the rotational movement of the pivot joint device in either pivotal direction.

* * * * *